(12) United States Patent
Boston et al.

(10) Patent No.: US 11,054,333 B2
(45) Date of Patent: Jul. 6, 2021

(54) DEVICE FOR DETECTING AN OIL LEAK

(71) Applicant: Caterpillar Inc., Deerfield, IL (US)

(72) Inventors: Samuel James Boston, Peoria, IL (US); Samuel Jaroslav Stafl, Peoria, IL (US)

(73) Assignee: Caterpillar Inc., Peoria, IL (US)

(*) Notice: Subject to any disclaimer, the term of this patent is extended or adjusted under 35 U.S.C. 154(b) by 131 days.

(21) Appl. No.: 16/354,268

(22) Filed: Mar. 15, 2019

(65) Prior Publication Data
US 2020/0292408 A1     Sep. 17, 2020

(51) Int. Cl.
| | |
|---|---|
| *G01M 3/04* | (2006.01) |
| *G01M 3/02* | (2006.01) |
| *G01M 3/16* | (2006.01) |
| *G01M 3/38* | (2006.01) |
| *G01N 33/28* | (2006.01) |
| *G08B 5/36* | (2006.01) |
| *G08B 21/18* | (2006.01) |
| *G08B 5/22* | (2006.01) |
| *G08B 21/20* | (2006.01) |

(52) U.S. Cl.
CPC .............. *G01M 3/04* (2013.01); *G01M 3/025* (2013.01); *G01M 3/047* (2013.01); *G01M 3/16* (2013.01); *G01M 3/38* (2013.01); *G01N 33/28* (2013.01); *G08B 5/36* (2013.01); *G08B 21/187* (2013.01); *G01M 3/02* (2013.01); *G08B 5/223* (2013.01); *G08B 21/20* (2013.01)

(58) Field of Classification Search
CPC .......... G01M 3/04; G01M 3/16; G01M 3/047; G01M 3/38; G01M 3/025; G01M 3/02; G08B 5/36; G08B 5/223–225; G08B 21/20; G08B 21/187
See application file for complete search history.

(56) References Cited

U.S. PATENT DOCUMENTS

| | | | |
|---|---|---|---|
| 3,719,936 A | 3/1973 | Daniels et al. | |
| 4,563,674 A | 1/1986 | Kobayashi | |
| 5,789,665 A | 8/1998 | Hedges et al. | |
| 5,974,860 A * | 11/1999 | Kuroda | G01M 3/38 |
| | | | 73/40 |

(Continued)

FOREIGN PATENT DOCUMENTS

| | | |
|---|---|---|
| CA | 2955710 | 8/2020 |
| CN | 105021358 A | 11/2015 |

(Continued)

OTHER PUBLICATIONS

English translation for EP-2669525 (Year: 2013).*

(Continued)

*Primary Examiner* — Peter J Macchiarolo
*Assistant Examiner* — Fatemeh Esfandiari Nia
(74) *Attorney, Agent, or Firm* — Hibshman Claim Construction PLLC

(57) ABSTRACT

A portable oil leak detection system having an oil sensor mountable to an engine and configured to detect the presence of oil and a processor positioned within a portable housing. The processor is configured to receive a signal indicative of the oil sensor detecting oil, record a timestamp in response to receiving the signal indicative of the oil sensor detecting oil, and activate an alert indicating that the oil sensor has detected oil.

18 Claims, 2 Drawing Sheets

(56) References Cited

U.S. PATENT DOCUMENTS

| | | | |
|---|---|---|---|
| 2010/0315246 A1* | 12/2010 | Gilpatrick | G01F 23/04 |
| | | | 340/623 |
| 2013/0220466 A1 | 8/2013 | Zandiyeh et al. | |
| 2017/0030528 A1* | 2/2017 | Dietzen | G08B 21/20 |
| 2017/0212004 A1 | 7/2017 | Suzuki | |
| 2018/0136075 A1* | 5/2018 | Lerman | G01M 3/20 |
| 2018/0149551 A1 | 5/2018 | Okajima | |
| 2018/0158261 A1* | 6/2018 | Ottikkutti | G07C 5/0816 |
| 2019/0375423 A1* | 12/2019 | Dudar | B60W 50/0205 |

FOREIGN PATENT DOCUMENTS

| | | | | |
|---|---|---|---|---|
| CN | 103822766 B | | 8/2016 | |
| CN | 106076918 A | | 11/2016 | |
| CN | 205981565 U | | 2/2017 | |
| EP | 1879008 | | 12/2009 | |
| EP | 2669525 A1 | * | 12/2013 | F04D 29/128 |
| JP | H0616011 B2 | | 3/1994 | |
| JP | 06241180 | * | 8/1994 | F04C 28/28 |
| JP | H08128916 A | | 5/1996 | |
| KR | 20150025605 | | 3/2015 | |

OTHER PUBLICATIONS

Liquid Leak Detection Sensor Type OSP, found at https://www.cmrelectrical.com/wp-content/uploads/2013/11/OSP-Leak-detection-Sensor.pdf; accessed on Jan. 31, 2019.

* cited by examiner

DEVICE FOR DETECTING AN OIL LEAK

TECHNICAL FIELD

The present disclosure relates generally to a device and process for detecting the presence of oil, and in particular, a portable device for detecting an oil leak on an engine.

BACKGROUND

Internal combustion engines employ various oil seals and gaskets to isolate the engine parts to be lubricated and prevent unwanted leaks. One such seal is the crankshaft rear main seal which keeps oil sealed inside the rear of the engine, where the crankshaft connects with the transmission, and prevents oil from leaking into the flywheel housing. Rear main seals can be made of rubber or silicone, and they can wear out because of age, the rotational forces of the crankshaft, corrosion from road salt, and other environmental factors. In addition, rear main seal leaks can result from improper installation of the rear main seal, defects in the seal, and defective, worn, pitted or degraded engine parts such as the main caps or the crankshaft itself.

Determining if a rear main seal leak exists and troubleshooting the leak usually requires taking the engine out of service and disassembling a portion of the powertrain, which can be costly and time consuming. To avoid the cost and downtime, some attempts have been made to implement real-time leak detection. For example, Chinese Utility Model CN205981565, entitled "Engine Oil Seal's Real-Time Leak Hunting Device", discloses a device including an EPDM rubber block, a pressure sensor, and a processor. The EPDM rubber block is mounted at a location on the engine such that oil leaking from the oil seal will fall or splash onto the EPDM rubber block causing it to swell. As the EPDM rubber block swells, it will press against the pressure sensor generating a pressure signal which is transmitted to the processor.

SUMMARY

The disclosure describes, in one aspect, a portable oil leak detection system having an oil sensor mountable to an engine and configured to detect the presence of oil and a processor positioned within a portable housing. The processor is configured to receive a signal indicative of the oil sensor detecting oil, record a timestamp in response to receiving the signal indicative of the oil sensor detecting oil, and activate an alert indicating that the oil sensor has detected oil.

The disclosure describes, in another aspect, a method for detecting an oil leak on an engine. The method includes positioning an oil sensor relative to the engine at a location where the oil sensor can detect an oil leak, detecting the presence of oil with the oil sensor and generating a signal indicative of detecting the presence of oil, activating a first alert in response to the signal indicative of detecting the presence of oil, and recording a timestamp in response to receipt of a signal indicative of detecting the presence of oil.

BRIEF DESCRIPTION OF THE DRAWINGS

Further features and advantages of the invention will become apparent from the description of embodiments using the accompanying drawings. In the drawings.

DETAILED DESCRIPTION

This disclosure relates to a system and method for detecting an oil leak on an internal combustion engine. In accordance with the present disclosure, the system can be utilized to detect an oil leak in a variety of applications utilizing an internal combustion engine, including mobile machines, such as for example, an excavator, a mining truck, an on-highway truck, an automobile, a locomotive, and a marine vessel, and stationary applications, such as for example, an engine-generator and a pump station. The system may be configured as a portable system that can be used in-field to detect an oil leak while the engine is running without pulling the engine out of service or disassembling a portion of the engine. The system can effectively detect oil leaks in real-time and, when an oil leak is detected, record an accurate timestamp and provide an alert. The system may be able to record the duration of the oil leak by providing a timestamp when oil is first detected and a timestamp when oil is no longer being detected.

Figure 1:
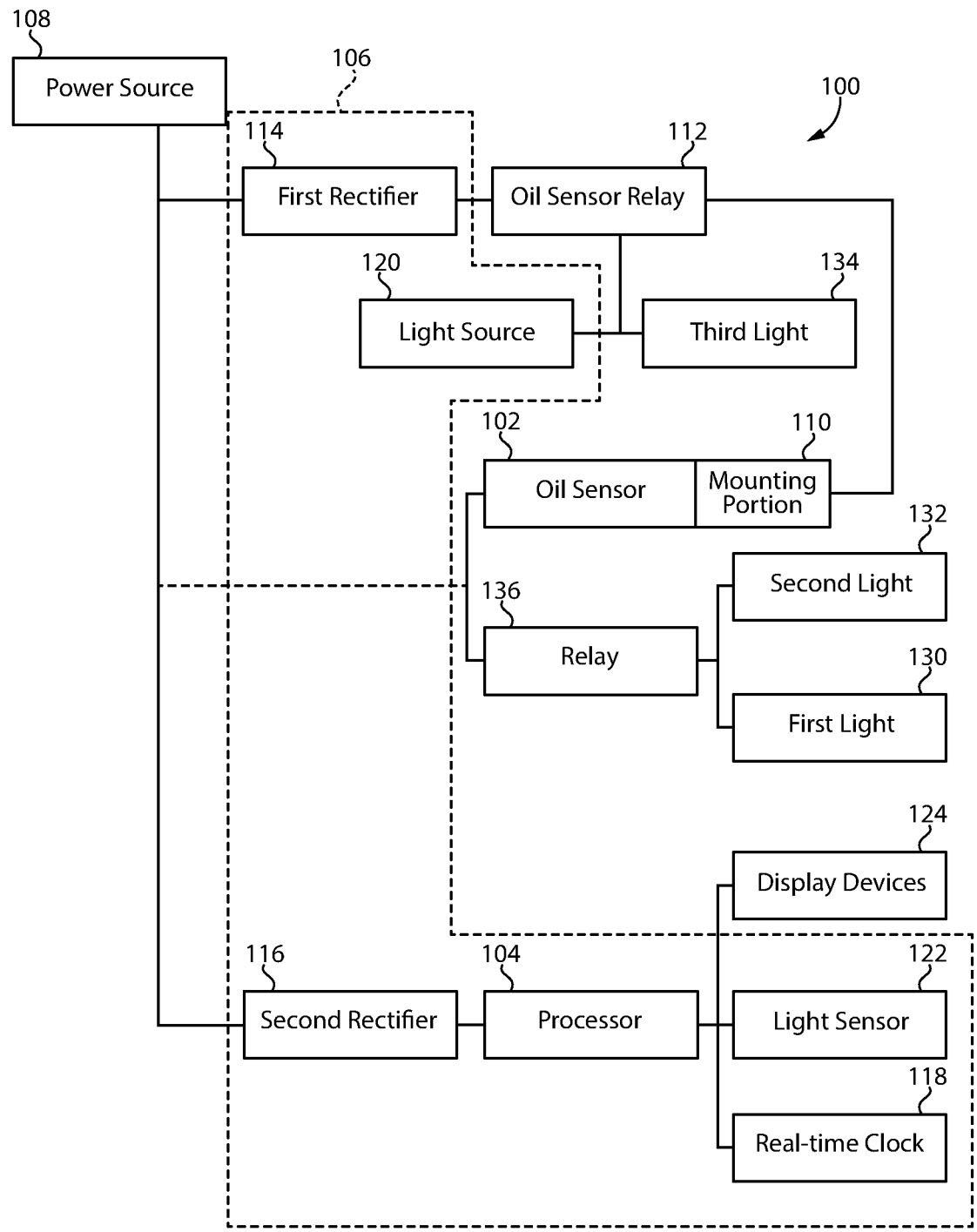
FIG. 1 is a schematic diagram of an exemplary embodiment of a device for detecting an oil leak.

FIG. 1 shows a schematic of an exemplary embodiment of a system 100 for detecting an oil leak. The system 100 may be configured in a variety of ways. For example, some embodiments may include one or more different components and/or may arrange the system components in different configurations than the components and configuration of the illustrated embodiment. Any combination of the above-described components and configurations in all possible variations thereof is encompassed by the disclosure unless otherwise indicated herein or otherwise clearly contradicted by context. In the illustrated embodiment, the system 100 includes an oil sensor 102 and a processor 104. The processor 104 may be positioned within a portable housing 106. A power source 108 may be associated with the system 100 to provide power for the system to operate. The power source 108 may be a system power source, such as for example, a battery (not shown) disposed within the housing 106 or an external power source, such as 120 VAC domestic power. In the illustrated embodiment, the system 100 includes a plug (not shown) for plugging into an electrical outlet to connect the system 100 to domestic power (120 VAC).

The oil sensor 102 can be configured in a variety of ways. Any sensing device capable of detecting the presence of oil and being mounted at a location on or adjacent an engine to detect an oil leak may be used. In the illustrated embodiment, the oil sensor 102 is an optical liquid sensor, but any suitable liquid or leak detecting sensor may be used. A suitable optical liquid sensor is the Liquid Leak Detection Sensor Type OSP from CMR Electrical Ltd.

The oil sensor 102 may be electrically coupled to the power source 108 to provide power to the oil sensor 102. The oil sensor 102 may also include a mounting portion 110 configured to mount the oil sensor 102 onto, or adjacent, an engine. The mounting portion 110 may be configured in a variety of ways. Any configuration that allows the oil sensor 102 to mount onto, or adjacent, an engine in a position to detect an oil leak may be used. The mounting portion 110, for example, can include threads allowing the oil sensor 102 to be screwed into a fitting, a bracket allowing the sensor to mount onto a surface, or other suitable attachment features or combinations thereof. In one embodiment, the mounting portion 110 may include threads configured to mate with corresponding threads on the drain plug port of the flywheel housing on the engine. Such a configuration allows the oil sensor 102 to thread into the drain plug port such that the oil sensor 102 is positioned to detect oil that has leaked from the crankshaft rear main seal of the engine.

In the illustrated embodiment, the system 100 includes an oil sensor relay 112 associated with the oil sensor 102. The oil sensor relay 112 may be any suitable electrically operated switch. The oil sensor relay 112 is operatively coupled to the oil sensor 102 and configured to open and close in response to the oil sensor 102 detecting oil or not detecting oil, respectively. The oil sensor relay 112 is electrically coupled to the power source 108.

In the illustrated embodiment, a first rectifier 114 is positioned between the oil sensor relay 112 and the power source 108. The first rectifier 114 can be any suitable rectifier for converting alternating current to direct current. In the illustrated embodiment, the first rectifier 114 is configured to convert 120 VAC to 24 VDC.

The processor 104 is configured to receive a signal indicative of the oil sensor 102 detecting the presence of oil, record a time stamp indicative of the time at which oil was detected by the oil sensor 102, record a time stamp indicative of the time at which oil is no longer being detected by the oil sensor 102, if applicable, and provide one or more alerts indicative that oil has been detected and/or is currently being detected. The processor 104 may be any suitable processor. The processor 104 can be a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor 104 may be any processor, controller, microcontroller, or state machine. The processor 104 may also be implemented as a combination of computing devices, for example, a combination of a DSP and a microprocessor, or any other such configuration. The processor 104 can include functions, steps, routines, data tables, data maps, charts and the like saved in and executed from any type of computer-readable medium, such as a memory device (e.g., random access, flash memory, and the like), an optical medium (e.g., a CD, DVD, BluRay®, and the like), firmware (e.g., an EPROM), or any other storage medium. In one exemplary embodiment, the processor 104 can be one or more small single-board microcontrollers and microcontroller kit computers, such as a Raspberry Pi® or Arduino® system.

The processor 104 is electrically coupled to the power source 108. In the illustrated embodiment, a second rectifier 116 is positioned between the processor 104 and the power source 108. The second rectifier 116 is similar to the first rectifier 114 but is configured to convert 120 VAC to 12 VDC to power the processor 104. The processor 104 includes, or is communicatively coupled to, a real-time clock 118 that the processor 104 can access to create and save into memory a time stamp of various events. The real-time clock 118 is electrically coupled to a system power source (not shown), such as a battery, positioned within the housing 106. The system power source for the real-time clock 118 is configured to power the real-time clock 118 to allow the clock to keep an accurate time even when the system 100 is not connected to the power source 108.

In one embodiment, the processor 104 creates and saves a time stamp for every instance that the oil sensor 102 detects an oil leak and for every instance the oil sensor 102 no longer detects an oil leak after having previously detected an oil leak.

In some exemplary embodiments, the processor 104 may be communicatively coupled to the oil sensor 102 to receive a signal from the oil sensor 102 indicative that oil has been detected. Thus, the processor 104 may be configured to act upon receipt of a signal from the oil sensor 102 or oil sensor relay 112. In the illustrated embodiment, however, the processor 104 is not directly communicatively coupled to the oil sensor 102 or oil sensor relay 112. Instead, in the illustrated embodiment, the system 100 includes a light source 120 and a light sensor 122, both positioned within the housing 106.

The light source 120 is electrically coupled to the oil sensor relay 112 and configured to turn on when the oil sensor 102 detects oil. The light sensor 122 is communicatively coupled to the processor 104 and configured to detect that the light source 120 has been activated and send a signal to the processor 104 indicative of the light source 120 being activated.

The light source 120 and the light sensor 122 can be any suitable light source 120 and light sensor 122 combination. In particular, the light source 120 must have sufficient luminance when activated to be detected by the light sensor 122 being used and the light sensor 122 being used must have sufficient sensitivity to detect that the light source 120 being used has been activated. In the illustrated embodiment, the light source 120 is an LED strip.

Suitable light sensors 122 include photoresistors, photodiodes, and phototransistors. In the illustrated embodiment, the light sensor 122 is a digital light sensor. The light sensor 122 is positioned and oriented within the housing 106 to detect whether the light source 120 has been activated.

The system 100 may also include one or more display devices 124 that are communicatively coupled to the processor 104 and configured to display various information to a user. The one or more display devices 124 may be configured in a variety of ways and can include any type of known display devices 124. In some embodiments, the one or more display devices 124 may also be configured to allow user input, such as for example, a touchscreen or the like. In the illustrated embodiment, the display device 124 is an LCD screen mounted to the exterior of the housing 106.

The system 100 may also include one or more alerts or indicators for providing an indication of a status of the system or the occurrence of one or more events. For example, the alerts or indicators may provide an indication that the system 100 is powered ON, that the oil sensor 102 is currently detecting oil, that the oil sensor 102 has detected oil during the test period even if the oil sensor 102 is no longer detecting oil, that a malfunction has occurred, or any other event or status. The alerts or indicators can be configured in a variety of ways. For example, the alerts and indicators can be visual, audio, tactile, or otherwise configured. The alerts and indicators can be, for example, a light, a buzzer, a bell, a vibration, a notification, email, or text message sent to a computing or mobile device, or other suitable alerts and indicators. The alerts and indicators could also be one or more actions, such as automatically shutting off the engine when a leak is detected or other suitable actions.

In the illustrated embodiment, the system 100 include a first light 130, a second light 132, and a third light 134. Each of the lights 130, 132, 134 may be mounted to the exterior of the housing 106 or in any other suitable location. The lights, 130, 132, 134 can be any suitable lights, such as LED lights. The size, shape, location, luminance, type, color, and other properties of the lights may vary in different embodiments.

The first light 130 and the second light 132 are operatively connected to a relay 136. The relay 136 may be any suitable electrically operated switch. In the illustrated embodiment, the relay 136 is electrically connected to the power source 108 and operatively coupled to the processor 104. The processor 104 is configured to open and close the relay 136. When closed, the relay 136 connects the first light 130 to the power source 108 to activate the first light 130 while the second light 132 is deactivated. When open, the relay 136 electrically connects the second light 132 to the power source 108 to activate the second light 132 while the first light 130 is deactivated. The third light 134 is operatively connected to the oil sensor relay 112. When closed, the oil sensor relay 112 electrically connects both the third light 134 and the light source 120 to the power source 108 to activate both the third light 134 and the light source 120. When open, the oil sensor relay 112 isolates both the third light 134 and the light source 120 from the power source 108.

The housing 106 may be configured and sized to be portable and easily transported. In the illustrated embodiment, the processor 104, the light source 120, the light sensor 122, the relay 136, the real time clock 118, and the first and second rectifiers 114, 116 are located within the housing. The LCD display 124, the first light 130, the second light 132, and the third light 134 are positioned on the exterior of the housing. In other embodiments, however, the system components may be otherwise located and mounted.

INDUSTRIAL APPLICABILITY

The disclosure is applicable to detecting an oil leak on an internal combustion engine. The disclosed system and method may be used to detect an oil leak in a variety of engine applications. For example, the engine may be associated with a mobile machine, such as an excavator, mining truck, on-highway truck, automobile, locomotive, marine vessel, or other mobile machine. The engine may alternatively be associated with a stationary application, such as a pumping station or engine-electrical generator. The below disclosed method is described in relation to detecting an oil leak at an engine's crankshaft rear main seal. It is contemplated, however, that the system and method can be used to detect an oil leak at a variety of locations on an engine. The system and method are capable of detecting an oil leak while the engine is running without removing the engine from service or disassembling a portion of the engine. In one exemplary embodiment, other than the oil sensor 102 and oil sensor relay 112, the other components of the system 100 are either mounted within the housing 106 or mounted onto the housing 106. The housing 106 is sized such that the system 100 is portable and can be easily moved to a location near or adjacent the engine.

Figure 2:
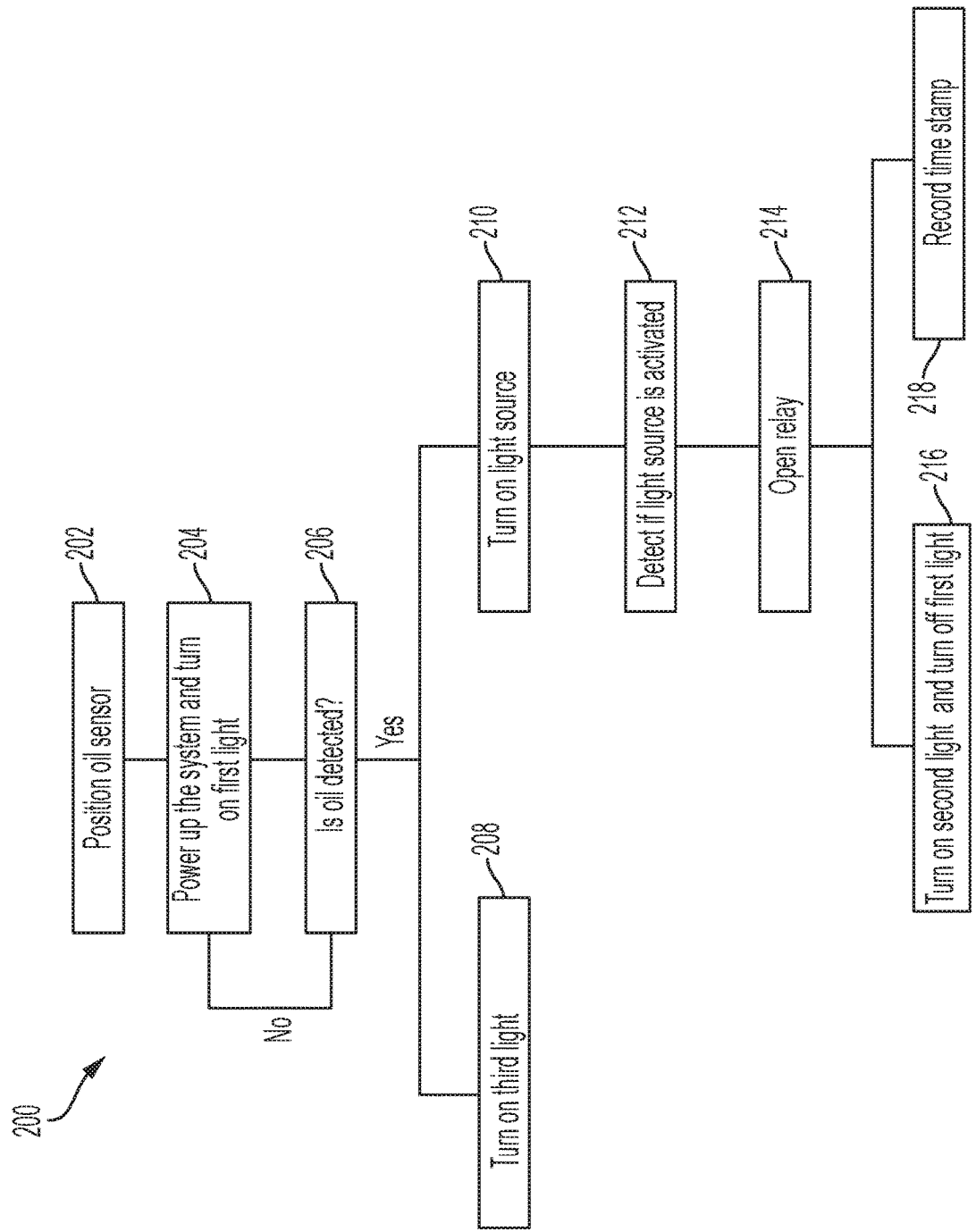
FIG. 2 is a flow diagram of an exemplary embodiment of a method for detecting an oil leak.

FIG. 2 illustrates a flowchart of an exemplary embodiment of a method 200 for detecting an oil leak. At step 202, the oil sensor 102 is positioned relative to an engine at a location where the oil sensor 102 can detect an oil leak. For example, the oil sensor 102 may be mounted to the engine or adjacent the engine. In one exemplary embodiment, the oil sensor 102 is threaded into a drain plug port on a flywheel housing of an engine such that the oil sensor 102 may detect oil leaking into the flywheel housing from the crankshaft rear main seal of the engine.

At step 204, the system 100 is powered up. For example, the system 100 may include an electrical plug that can be inserted into an electrical outlet to provide access to domestic 120 VAC power. When the system 100 is powered on and the oil sensor 102 is activated but not detecting oil, the oil sensor relay 112 is in an open state and the third light 134 and the light source 120 are off or deactivated. In addition, the relay 136 is in a closed state and the first light 130 is on or activated and the second light 132 is off or deactivated. Thus, the first light 130 may act as an indicator or alert that the system 100 is powered up and no oil is currently being detected. While the engine is running, the oil sensor 102 is activated and sensing for the presence of oil in the flywheel housing.

At step 206, if the oil sensor 102 does not detect oil, it will continue to monitor for the presence of oil at step 204. If the oil sensor 102 does detect oil, the oil sensor relay 112 will change from an open state to a closed state and rout power to the third light 134 and the light source 120 to turn both the third light 134 and the light source 120 on, in step 208 and step 210 respectively. In one exemplary embodiment, the third light 134 and the light source 120 are turned on simultaneously or nearly simultaneously. Thus, the third light 134 may act as an indicator or alert that oil is currently being detected.

At step 212, the light sensor 122 detects that the light source 120 is now on and sends a signal indicative of the light source being on (and the oil sensor detecting oil) to the processor 104. At step 214, the processor 104 receives the signal from the light sensor 122 and opens the relay 136. The relay 136, when opened, routes power to the second light 132 and stops routing power to the first light 130 such that the second light 132 turns on and the first light 130 turns off at step 216. In the exemplary embodiment, once oil has been initially detected, the processor 104 will maintain the relay 136 in the open state and the second light 132 will remain on even if oil is no longer being detected. Thus, the second light 132 may act as an indicator or alert that oil has, at some point during the test, been detected.

At step 218, when the processor 104 receives the signal from the light sensor 122, the processor 104 will also record and store in memory a time stamp, as indicated by the real-time clock 118, indicative of the time at which the oil sensor 102 detected oil. In some embodiments, in addition to the lights 130, 132, 134, the system 100 may provide additional, or alternative, indicators or alerts indicative of the oil sensor detecting oil. For example, the system 100 may be configured to provide push notifications, text messages, or emails to a mobile device.

The oil sensor 102 will continue to sense for the presence of oil in the flywheel housing. If the oil sensor 102 no longer detects oil in the flywheel housing, the oil sensor relay 112 will change from the closed state back to the open state resulting in both the third light 134 and the light source 120 to turn off.

Once the light source 120 turns off, the light sensor 122 ceases sending the signal to the processor 104. In response to the lack of signal from the light sensor 122, the processor 104 records and stores in memory a time stamp, as indicated by the real-time clock 118, indicative of the time at which the oil sensor 102 no longer detected oil. As indicated earlier, however, the processor 104 maintains the relay 136 in the open state and the second light 132 will remain on even if oil is no longer being detected.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

ELEMENT LIST

| Element Number | Element Name |
| --- | --- |
| 100 | system |
| 102 | oil sensor |
| 104 | processor |
| 106 | portable housing |
| 108 | power source |
| 110 | mounting portion |
| 112 | oil sensor relay |
| 114 | first rectifier |
| 116 | second rectifier |
| 118 | real-time clock |
| 120 | light source |
| 122 | light sensor |
| 124 | display devices |
| 130 | first light |
| 132 | second light |
| 134 | third light |
| 136 | relay |
| 200 | method |
| 202 | step |
| 204 | step |
| 206 | step |
| 208 | step |
| 210 | step |
| 212 | step |
| 214 | step |
| 216 | step |
| 218 | step |

What is claimed is:

1. A portable oil detection system, comprising:
   an oil sensor mountable to an engine and configured to detect a change in a presence of oil;
   a processor positioned within a portable housing, the processor being configured to:
   receive a signal indicative of the oil sensor detecting the change in the presence of oil;
   record a timestamp in response to receiving the signal indicative of the oil sensor detecting the change in the presence of oil; and
   activate an alert indicating that the oil sensor has detected oil; and
   a light source and a light sensor disposed within the portable housing, wherein the light source is configured to turn on in response to the oil sensor detecting oil, and wherein the light sensor is configured to generate a signal indicative of the light source being on.

2. The portable oil detection system of claim 1, wherein the oil sensor is an optical liquid sensor.

3. The portable oil detection system of claim 1, wherein the oil sensor is further configured to thread into a drain plug port on a flywheel housing.

4. The portable oil detection system of claim 1, wherein the signal indicative of the oil sensor detecting oil received by the processor is the same as the signal indicative of the light source being on generated by the light sensor.

5. The portable oil detection system of claim 1, wherein the light source is an LED strip.

6. The portable oil detection system of claim 1, wherein the alert is a light mounted onto the portable housing.

7. The portable oil detection system of claim 6, wherein the light does not turn off in response to the oil sensor no longer detecting oil.

8. The portable oil detection system of claim 6, further comprising a second light mounted onto the portable housing, the system being configured to turn on the second light when the oil sensor is detecting oil and turn off the second light when the oil sensor is not detecting oil.

9. A method for detecting an oil leak on an engine, the method comprising:
   positioning an oil sensor relative to the engine at a location where the oil sensor can detect the oil leak;
   detecting a presence of oil with the oil sensor and generating a signal indicative of detecting the presence of oil;
   activating a light source within a housing in response to the signal indicative of detecting the presence of oil;
   activating a first alert in response to the signal indicative of detecting the presence of oil; and
   recording a timestamp in response to receipt of a signal indicative of detecting the presence of oil.

10. The method of claim 9, wherein positioning the oil sensor further comprises threading the oil sensor into a drain plug port of a flywheel housing on the engine.

11. The method of claim 9, wherein the light source is an LED strip.

12. The method of claim 9, further comprising detecting the activation of the light source and generating a signal indicative of the light source being activated.

13. The method of claim 12, further comprising recording the timestamp is in response to a signal indicative of the light source being activated.

14. The method of claim 9, further comprising turning on a light mounted to an exterior of the housing simultaneously with activating the light source within the housing.

15. The method of claim 9, wherein activating the first alert comprises turning on a light.

16. The method of claim 15, further comprising activating a second light in response to the signal indicative of the light source being activated.

17. The method of claim 9, further comprising creating a time stamp indicative of the oil sensor no longer detecting the presence of oil.

18. The method of claim 9, wherein the oil sensor is an optical oil sensor.

* * * * *